US 7,644,632 B2
Jan. 12, 2010

(12) United States Patent
Best

(10) Patent No.: US 7,644,632 B2
(45) Date of Patent: Jan. 12, 2010

(54) VISCOMETRIC FLOWMETER

(76) Inventor: John W. Best, 805 Stratford Dr., Apt. 15, State College, PA (US) 16801

( * ) Notice: Subject to any disclaimer, the term of this patent is extended or adjusted under 35 U.S.C. 154(b) by 709 days.

(21) Appl. No.: 11/329,768

(22) Filed: Jan. 11, 2006

(65) Prior Publication Data
US 2006/0157392 A1 Jul. 20, 2006

Related U.S. Application Data

(60) Provisional application No. 60/643,877, filed on Jan. 15, 2005.

(51) Int. Cl.
G01F 1/86 (2006.01)
(52) U.S. Cl. .................................. 73/861.01
(58) Field of Classification Search .............. 73/54.02, 73/23.24, 861.01
See application file for complete search history.

(56) References Cited

U.S. PATENT DOCUMENTS

| 2,811,690 | A | 10/1957 | Sargent |
| 3,581,566 | A | 6/1971 | Goff et al. |
| 3,754,201 | A | 8/1973 | Adams |
| RE29,393 | E | 9/1977 | Becker |
| 4,147,298 | A | 4/1979 | Leemhuis |
| 4,397,190 | A | 8/1983 | Hulin |
| 4,475,407 | A | 10/1984 | Kruncos |
| 4,641,535 | A | 2/1987 | Malguarnera |
| 4,745,800 | A | 5/1988 | Henning |
| 4,817,022 | A | 3/1989 | Jornod et al. |
| 5,081,448 | A | 1/1992 | Yoshii |
| 5,515,295 | A | 5/1996 | Wang |
| 5,544,531 | A | 8/1996 | Heckman |
| 5,755,559 | A | 5/1998 | Allington et al. |
| 5,902,927 | A | 5/1999 | Titus |
| 5,905,208 | A | 5/1999 | Ortiz et al. |
| 6,532,802 | B2 | 3/2003 | Paul et al. |
| 6,532,828 | B1 * | 3/2003 | Delsing .................... 73/861.01 |
| 6,536,271 | B1 | 3/2003 | Gopalakrishnan et al. |
| 6,536,291 | B1 | 3/2003 | Gysling et al. |
| 6,604,054 | B2 | 8/2003 | Lipscomb et al. |
| 6,648,609 | B2 | 11/2003 | Berger et al. |
| 6,658,946 | B2 | 12/2003 | Lipscomb et al. |
| 6,687,643 | B1 | 2/2004 | Cason, Jr. |
| 6,691,584 | B2 | 2/2004 | Gysling et al. |
| 6,712,085 | B2 | 3/2004 | Weissgerber et al. |
| 6,745,135 | B2 | 6/2004 | Keilty et al. |
| 6,889,562 | B2 | 5/2005 | Gysling et al. |
| 2002/0194932 | A1 | 12/2002 | Gysling et al. |
| 2003/0172744 | A1 | 9/2003 | Matsuzawa et al. |
| 2005/0005710 | A1 | 1/2005 | Sage, Jr. |

* cited by examiner

Primary Examiner—Hezron Williams
Assistant Examiner—Alex Devito

(57) ABSTRACT

A meter for reproducibly and accurately measuring the delivery or flow rate of known fluids in chromatography and other pressure driven pumping systems, comprising a sense tube of known effective radius and length, coupled to a temperature measuring device, and enclosed in such a way as to allow the temperature of the tube and fluid to be measured, and optionally regulated. The invention is also useful for determining the viscosity of an unknown fluid or combination of fluids.

14 Claims, 6 Drawing Sheets

VISCOMETRIC FLOWMETER

RELATED APPLICATIONS

This application claims priority to U.S. Provisional Patent Application No. 60/643,877 filed Jan. 15, 2005.

BACKGROUND OF THE INVENTION

The present invention relates generally to the fields of Liquid Chromatography (LC), High Performance Liquid Chromatography (HPLC), and preparative chromatography, and comprises a method and apparatus for the accurate and precise measurement of all parameters which affect the quality of the delivery of pressure-driven liquids in an LC or HPLC system. In particular, the invention relates to a method and apparatus for precisely measuring fluid flow rate in such a way as to provide visibility of both short and long term deviations of the flow rate of liquids in LC or HPLC systems.

Liquid chromatography is a widely used technique for separating complex mixtures of chemicals into their constituent parts. This is accomplished by pumping the mixture (mobile phase) through a separation device referred to as a "column." More specifically, an LC (Liquid Chromatography) column is a cylindrical tube containing a separation media (stationary phase). The separation media is porous so that the mixture will pass through it. As the mixture passes through, the separation media selectively impedes or slows the flow of the various components that make up the mixture. The desired outcome is that those constituents that are less restricted by the separation media exit the column (elute) sooner than more restricted components, which travel at a lower speed through the column.

At its simplest level, an LC system consists of only two components: a pump and an LC column. In practice, however, commercial LC systems often comprise multiple pumps, columns, specialized detectors which are sensitive to the eluents, various fluid handling valves, and sophisticated software for controlling the process and collecting data. It is the mission of many manufacturers to provide sophisticated and consistent LC columns, chemicals, methods, and other necessary equipment in order to achieve consistent separation of the mobile phase into very distinct eluents.

In any LC system, the most fundamental parameter that must be controlled is the flow rate of fluids through the system. The flow rate results from pressure which is applied by the LC pump. It follows in practice that most flow consistency and accuracy issues originate because of the fundamental character of the pump. The majority of LC pumps are cam driven piston pumps, typically having one or two pistons, a fluid inlet, and a fluid outlet. The fluid inlet is typically at or near atmospheric pressure, and the fluid outlet is typically at a high pressure. Outlet pressures can be as high as 5000 PSI, and recently introduced pumps have pushed this limit to approximately 15,000 PSI.

To achieve these pressures, a rotating cam applies force to a high strength piston. Each piston operates in a reciprocating fashion. As the piston moves forward, fluid is pressurized and exits the pump, to be driven through the rest of the LC system. When the piston reaches the end of its stroke, it is retracted as it follows the profile of the rotating cam, and the cylinder is refilled with fluid to be delivered on the next forward stroke. A check (one way) valve is used to keep fluid which has been pushed out of the pump from reentering the pump on the refill stroke. A second check valve keeps fluid which is pressurized by the piston from flowing back out through the pump inlet.

In practice, all piston driven pumps have two intrinsic characteristics that can cause them to provide anomalous deviations in flow rate. It is the common goal of LC system manufacturers to minimize the deleterious effect caused by these characteristics. The first characteristic is visualized by considering a single piston pump. Flow deviation occurs as the piston is being retracted and the cylinder is refilling. During this time, no fluid is delivered from the pump. The lack of additional fluid to compensate for the normal loss of fluid through the LC column causes a momentary pressure drop. This causes the separation and elution processes to slow down until the pump is again delivering fluid at the correct pressure.

Manufacturers offer dual piston pumps as a solution to the above-mentioned anomaly. Ideally, when one piston is refilling, the second piston is delivering fluid, thus eliminating the momentary pressure drop. In practice, a second less apparent anomaly occurs during the changeover from one piston to the other, and is typically masked by the refill pulse in the case of the single piston pump.

The second anomaly is the result of the relationship between the exact moment the outlet check valve(s) open, the desired working system pressure, and a physical characteristic of all fluids, namely, compressibility. Since a check valve opens when the pressure on the inlet side is greater than the pressure on the outlet side, it is necessary to expend some of the piston's stroke to achieve an internal pump pressure equal to the system pressure. This fraction of a stroke is referred to as "pre-compression." The amount of stroke lost to pre-compression increases as the overall desired system pressure is increased. If the pump or system does not specifically and correctly compensate for the required pre-compression, the flow rate will be incorrect. In other words, a dip or a spike in pressure (and thus flow rate) can result, depending on whether pre-compression compensation is set above or below the required operating pressure to achieve the required flow rate.

With regard to this second anomaly, a very practical consideration is: as an LC column ages, the required pressure to achieve a given flow rate typically increases. Therefore, an LC system that is properly pre-compensated for a new column will suffer degradation in elution consistency if the pre-compensation is not adjusted with regard to the required flow vs. pressure characteristic of the aging column.

A solution to both of these anomalies is available in the form of a pressure reservoir, which is inserted in the hydraulic system at some point between the pump and the LC column. This reservoir stores fluid that is compressed to the operating pressure of the LC column. When a deviation of flow results from the pump, the reservoir absorbs or releases fluid as determined by the size of the reservoir, the actual pressure, and the rate of fluid loss through the column and other hydraulic components. The effect is to lessen the severity of the flow deviation by providing a longer decay time. The pressure decay is exponential, and is according to the formula:

$$P(t) = Ps * e^{-(t/RC)}$$

Where:
P(t)=the resulting pressure as a function of time
Ps=the system pressure when the piston refill begins
e=2.71828
t=time
R=resistance to flow or backpressure generated by column to flow
C=capacity in PSI/mL of the pressure reservoir In practice, a reservoir is sized to allow an acceptable deviation of pressure at a given operating condition (flow rate and pressure). The trend towards conducting HPLC analysis at lower flow rates is significant with respect to the technique of using a pressure reservoir. The problem lies in attempting to decrease flow rate by simply slowing the rotation of the pump's cam. This approach causes the refill time to be extended inversely with the reduction of flow rate. During refill, system pressure decays exponentially with time. A typical reduction in flow rate will result in a longer period of time in which pressure decay will occur. This allows a system to fall below the flow deviation requirements of the original system design. By way of example, if a pump that is optimized to provide 1% deviation in flow at 100 μL/min is operated at 10 μL/min, a 37% deviation will result. This is true of pumps using mechanically connected cams (driven by a single motor) to drive the pistons, because the refill stroke cannot be altered without affecting the opposing piston's fill stroke. In the case of single piston pumps, there is some ability to increase the speed of the refill stroke and the precision of refill stroke timing by using the inverse of the desired reduction of flow rate.

Other means of driving pistons such as motorized linear screw drives are also available, which can vary the pre-compression appropriately for the fluid and operating pressure. In such case, however, it is still advisable to monitor pulsation performance to verify that the pump has been calibrated and compensated correctly, and is not malfunctioning.

The net effect of the foregoing problem is that eluents do not arrive at the output of the LC column at consistent times, and there is a possibility of the eluents themselves being misclassified. Additional analysis, typically through mass spectroscopy, is often necessary to resolve doubts that occur due to inconsistencies in elution resulting from flow rate fluctuation.

A common method of attempting to correct the aforementioned problem; that is, the inability to simply slow cam-driven pumps to achieve lower flow rates, is called "flow splitting," or simply "splitting." Referring to FIG. 3, the topology of a flow splitting system is apparent. In this topology, the pump is operated at a flow rate that is within its proven performance range. The output of the pump drives a three-way "T" type junction. Of the two remaining connections of the T-junction, one is connected to the column; the remaining connection drives a backpressure control device. By adjusting the amount of backpressure on the non-column output of the T, the flow through the column can be controlled.

A serious fundamental problem with this approach, however, is that the backpressure of the column itself varies over time, typically increasing as the column ages. As the column backpressure changes, it is necessary that a corresponding change occur in the regulating output of the T, otherwise column flow will be adversely affected. Even in the presence of either automatic or manual adjustment of the backpressure regulation means, the overall backpressure encountered by the pump changes, potentially shifting its operating point into a pressure range that is undesirable.

As of yet, there is no economical means to characterize column backpressure with regard to flow rate; or to measure the column flow rate on the high pressure side of the column when using a conventional cam-driven pump; or to quantify flow deviation as a function of time and pump operating pressure; or to alert a user as to the presence of adverse operating conditions; or to collect pressure and flow data from an independent device which can be used to validate system performance in the absence of any anomaly.

What is required is an instrument that can be inserted in the fluid path that will report pump pressure, column pressure, fluid temperature and flow data at adequate data rates to observe short term deviations in flow rate. Further, such a system should provide data in a readily readable form to a host PC, Personal Digital Assistant (PDA), laptop, or other programming device, which is capable of capturing and recording data relative to an accurate and independent time base.

Outside the field of the invention, there are many well known methods to determine flow rate, where the rate is comparatively large (>10 mL/minute). These include, for example, the use of turbine wheels, ultrasonic measurement of the velocity of bubbles or solids in a fluid stream, and displacement of a sphere or other indicator suspended within a vertical cone shaped fluid path. None of these methods are viable below sub-mL/minute (e.g. μL/m and nL/m) ranges of flows. Furthermore, none of the methods are suitable to advance the state-of the-art in LC or HPLC because they do not have adequately fast sampling rates to measure short term flow fluctuations.

Historically, liquid flow rates have been measured using a volumetric measuring device (graduated cylinder, pipette, syringe, etc.) and a means of measuring elapsed time. Using the measuring device, an operator typically observes the change in a fluid level or the movement of a trapped bubble to determine the fluid volume that flowed at a given time. The primary disadvantage of this method is that it does not allow adequate time resolution to detect or quantify sufficiently short term deviations in flow. Such deviations typically result from piston pumps and incorrect compensation for compressibility of the liquid being pumped, as has been described hereinabove.

A recently developed method uses two nano-fabricated thermistors placed along the fluid path, and a small heating element positioned near the upstream thermistor. As flow rate increases, there is a proportional increase in the amount of heat which must be applied to attain a constant temperature differential. This "thermal gradient" approach does allow the measurement of short term deviation of flow, but disadvantageously does not allow either a wide dynamic range or optimum insertion of the flowmeter in the flow path due to inability of the thermal gradient type flowmeter to withstand high operating pressures greater than a few hundred PSI.

An additional modern approach uses a pressure drop as a factor in determining flow. A shortcoming of this approach, however, is that the pressure drop is measured across a porous bed (see, e.g., U.S. Pat. No. 6,532,802). Thus the effect of variation of viscosity with temperature is not taken into account. Moreover, the possibility of change in the backpressure characteristic of the flow sensing element is more likely with a porous bed.

The prior art literature and patents describe a variety of methods for remediating flow deviation and pre-compression. However, the drawbacks to the traditional thermal sensing flowmeters illustrate the need for alternatives or improvements in controlling flow deviation and pre-compression in a hydraulics system. These are the primary needs addressed by the present invention.

SUMMARY OF THE INVENTION

The following are selected objects of the present invention:

It is an object of the present invention to provide an apparatus for the accurate and precise measurement of fluid parameters in a hydraulics system, regardless of the operating pressure of the system, up to a rated maximum pressure. "Fluid parameters," as used herein, include viscosity, pressure, temperature, flow direction, flow rate, and deviations in same.

It is a further object to provide an apparatus for the accurate and precise measurement of fluid parameters in an LC or an HPLC system.

It is yet another object of the invention to provide a readily visible indication of flow and/or pressure deviation to assist in verifying and validating LC and HPLC fluid delivery rates.

A further object of the invention is to provide a means to determine the effective or relative viscosity of a fluid of mixed or unknown composition.

Yet another object of the invention is to provide a means to alert a user or supervisory software if a safety or performance limit of the system has been reached.

Another object of the invention is to provide an apparatus having a control signal to allow for measurement and control of the flow rate of liquids in a high pressure system.

Other objects of the invention will be readily apparent from the following description of the invention and the related drawings.

The system and method of the present invention are implemented by measuring the pressure drop across a semi-rigid tube, as well as the temperature of a fluid within the tube. The tube, referred to herein as a "sense tube," is straight, curved, or coiled in shape, and is disposed at the outlet of a high pressure pumping means. Pressure measurement transducers are disposed at the inlet and outlet of the sense tube. The instantaneous viscosity of the fluid is determined through temperature measurement, application of suitable pressure and temperature corrections for the viscosity of the solvent or fluid being pumped, and application of an equation to determine the flow rate of the pumped liquid.

The present invention achieves superior performance, including operation across a wide range of pressures and temperatures, higher dynamic range, faster response and higher reliability over a wide range of flow rates, e.g. tens of nanoliters per minute (nL/min) to liters per minute (L/m).

BRIEF DESCRIPTION OF THE DRAWINGS

In the accompanying drawings, which are incorporated into and form a part of the disclosure of the invention, like elements are referred to by like numbers.

DETAILED DESCRIPTION OF THE INVENTION

The present invention comprises a system and a method for reproducibly and accurately measuring the parameters that affect the flow of liquids in pressure-driven pumping systems. By way of example, the system can be used to determine pressure, temperature, flow, and other parameters in liquid chromatography (LC), which includes preparative chromatography and high performance liquid chromatography (HPLC) systems. Pressures in HPLC can be very high (up to 20,000 PSI) and flow rates can be extremely low (below μL/min) and thus difficult to measure accurately and control under the best of conditions. The system is such that it can advantageously be used to provide data for feedback and control of pumps or other devices which directly impact the fluid delivery required for liquid chromatography/mass spectrometry (LC/MS) systems.

Using a temperature dependent viscosity factor for the desired fluid and the radius and length of a tube, said radius and length preferably also being temperature compensated, then, by measuring the pressure drop across the tube, which is disposed between a pumping system and a chromatography column, it is possible to accurately determine the flow rate of a fluid flowing from a pump into a chromatography column. Stated otherwise, such tube of known effective radius and length, coupled to a temperature measuring device, becomes a device for accurately measuring the flow rate of a fluid being delivered by a pressure-driven pumping system into a chromatography column. Since the pressure differential is proportional to viscosity, and viscosity varies with temperature, it is necessary to make a determination of viscosity based on the type of fluid and the temperature of same. In view of the aforementioned relationship, the flow rate measuring device of the present invention will hereinafter be referred to as a "Viscometric Flowmeter" 16.

Figure 2:
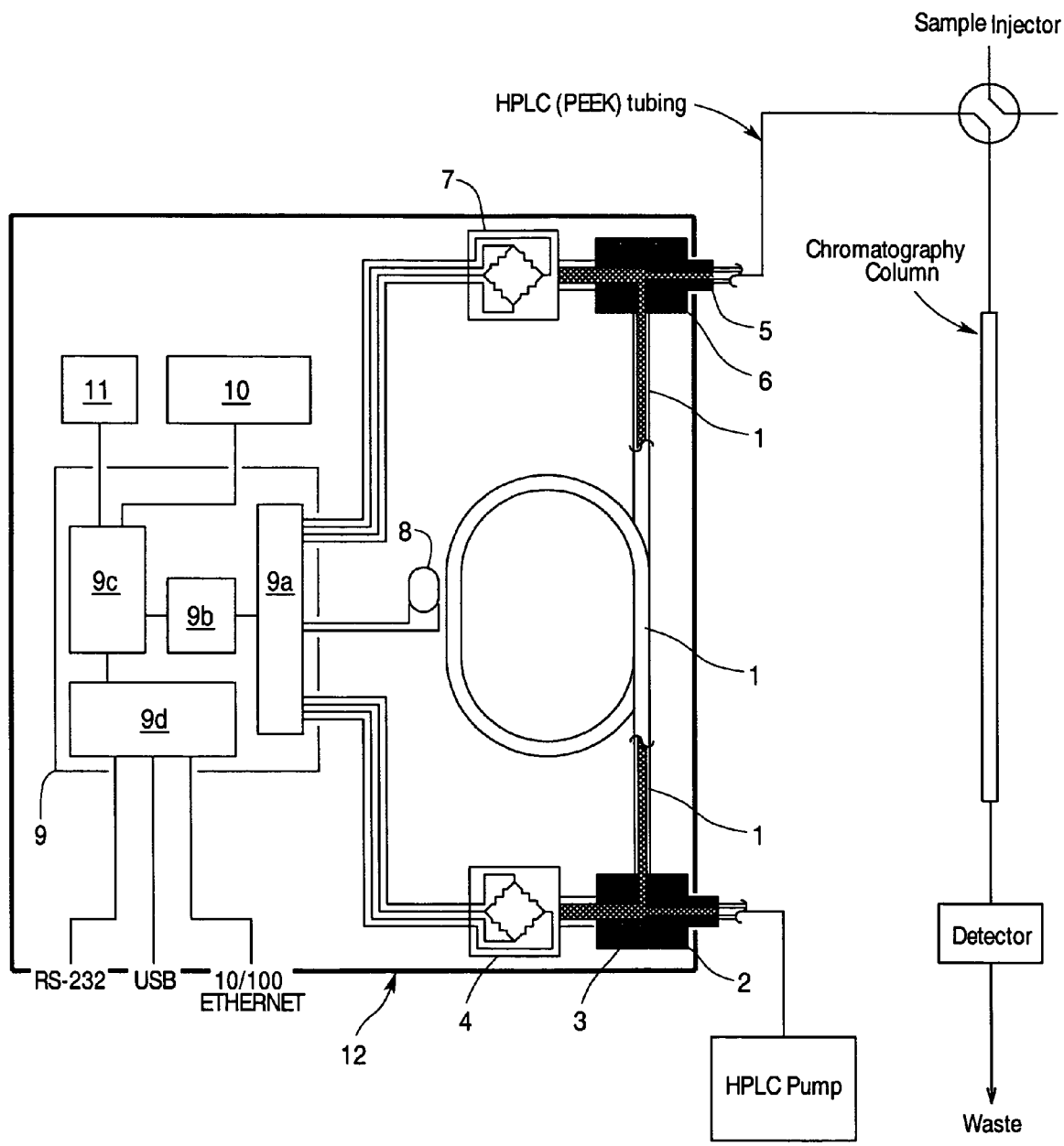
FIG. 2 is a schematic of the major internal components of an embodiment of the present invention, relative to the hydraulic path of a simple chromatography system.

Referring to FIG. 2, the internal hydraulic layout of an embodiment of the Viscometric Flowmeter 16 relative to the hydraulic path of a simple chromatography system is shown. The internal components handling the passage of fluids, in order of progression of the flow through the Flowmeter, include: fluid inlet 2, inlet manifold 3, first compression fitting 17, semi-rigid tube 1 (referred to herein as a "sense" tube), second compression fitting 17, outlet manifold 6, and fluid outlet port 5. It will be understood that although the sense element 1 is typically inserted at the output of a chromatography pump, the tube may be connected anywhere in a hydraulic system, as the embodiment shown in FIG. 2 can operate at temperatures in excess of 5000 PSI.

As shown, the fluid inlet port 2 is a part of the inlet manifold 3, a three-way hydraulic connection at the fluid input of the Flowmeter 16. The manifold 3 has internal passageways that connect the inlet port 2 from the external fluid path to an inlet pressure sensing transducer 4 and sense tube 1. The internal passageways of the inlet manifold 3 comprise holes which have a large radius compared to the inner diameter of the sense tube 1 to minimize pressure drop across the manifold. In a preferred embodiment, the inlet manifold 3 is fabricated of Polyetheretherketone (PEEK™). However, Type 316 stainless steel, titanium, or other high strength and suitably inert material may be used for fabrication of the manifold.

Connected to one end of the fluid inlet manifold 3 by means of a compression fitting 17 is a sense tube 1. The sense tube 1 is provided with pressure measuring means at both the inlet and outlet ports 2, 5 for measuring the absolute pressures thereof. The sense tube 1 is able to withstand typical operating pressures (in excess of 5000 PSI) with minimal deformation. As discussed herein, the pressure differential is corrected for fluid viscosity to provide flow rate data which is accurate and reproducible.

The sense tube 1 can be readily scaled to provide a wide range of flow monitoring and control solutions ranging from nanoliters per minute (nL/min) to liters per minute (L/min). As an example, to achieve a useable flow range of about 0.010 to 500 μL/min, a sense tube should be designed to have a length of approximately 3 to 5 feet and an inner diameter of about 0.0015 to 0.003 inches. In the same way, the geometry of the sense tube 1 can be suitably modified to shift the measuring range (nL/min to L/min) of a desired application.

For operation in conjunction with a chromatography column, it is desirable that the material that comprises the sense tube 1 be selected such that no contamination of the mobile phase occurs, and no degradation of the invention by solvents (that constitute a notable fraction of the mobile phase) occurs.

Thus the tubing material suitably comprises a plastic such as PEEK™. As an alternative, Type 316 stainless steel, titanium, PEEKSIL™, fused silica, or other high strength tubing may be employed in embodiments of the invention that are optimized for high flow rates or higher operating pressures (e.g. where the system pressure exceeds 5000 PSI).

At the end of the sense tube 1 that is connected to the inlet manifold 3 is the fluid inlet port 2, or high pressure side. An opposite (second) end of the sense tube 1, the lower pressure or outlet side, is connected by a compression fitting 17 to the fluid outlet manifold 6, of which the outlet port 5 is a part. Fluid is channeled from the low pressure side of the tube 1 to the exterior of the Flowmeter 16. In the embodiment shown in FIG. 2, the outlet port 5 of the Flowmeter is connected to a sample injection valve, then to an LC column, and finally to a detector.

A temperature sensitive transducer 8 (thermistor, thermocouple, etc.) is generally positioned in close proximity to the sense tube 1 to allow good thermal contact to be made therewith. The transducer 8 produces an electrical signal proportional to the temperature of the sense tube 1, thermal mass, or internal temperature of the Flowmeter 16, which is nearly identical to the temperature of the fluid. In a preferred embodiment of the invention, the transducer 8 and a portion of tube 1 within about 10 mm of the transducer are encapsulated together using an insulating agent to further improve temperature accuracy. In a more preferred embodiment, the constituents of the Flowmeter 16 are mounted within a housing 12 for optimal thermal insulating effect.

Figure 1A:
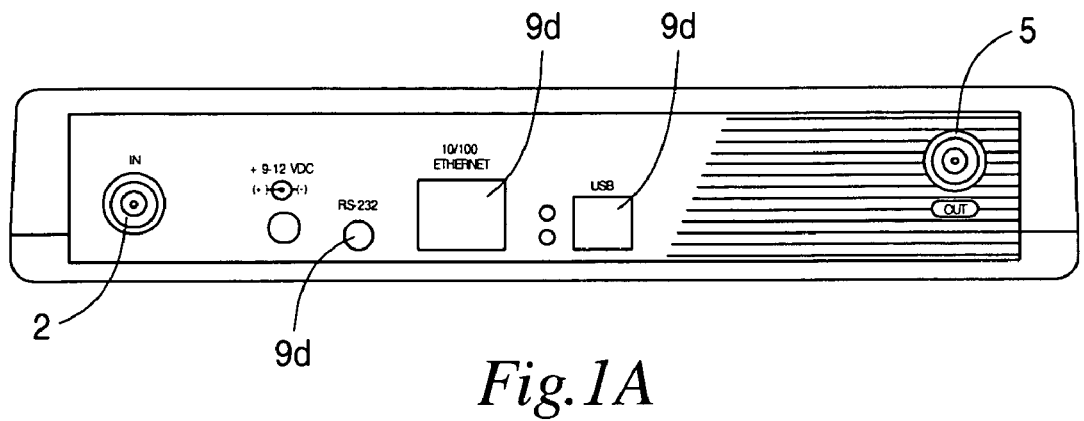
FIG. 1A is a rear, isometric view of an embodiment according to the present invention.
Figure 1B:
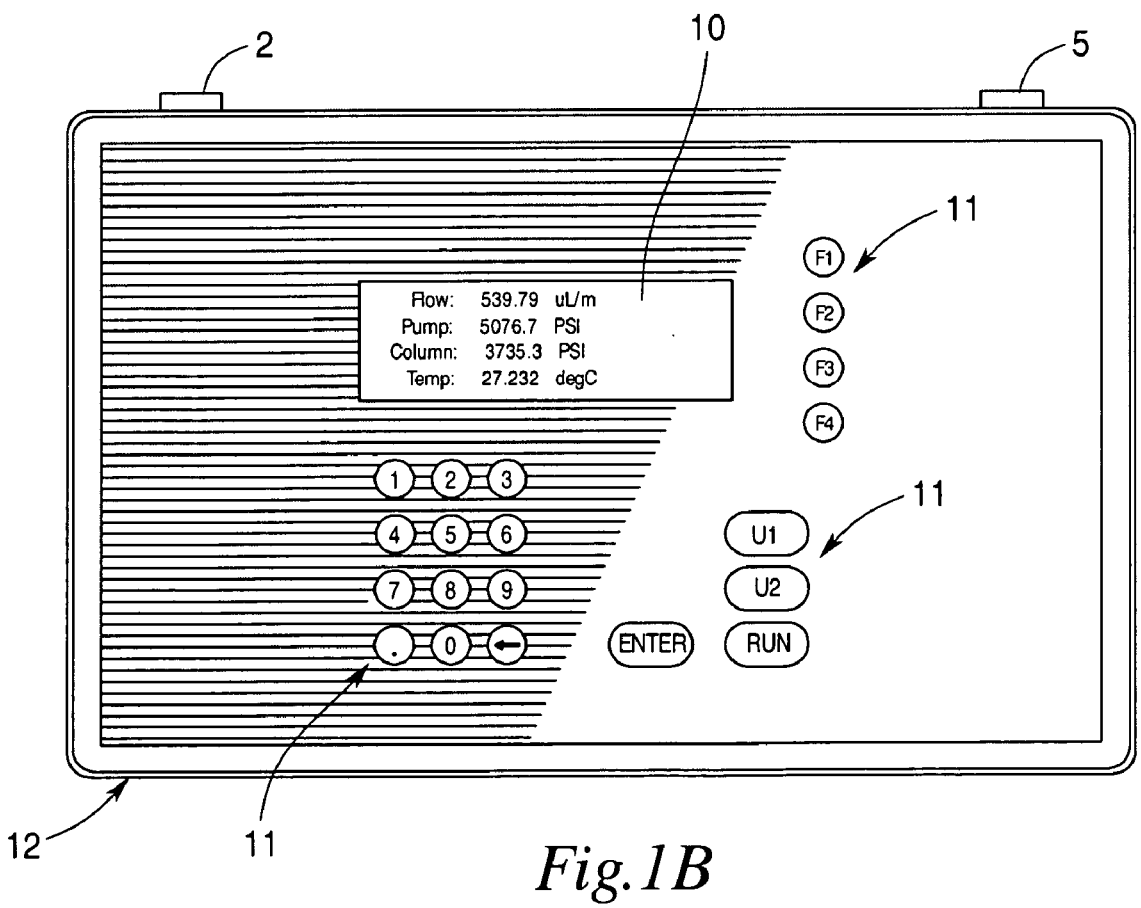
FIG. 1B is a top view of an embodiment of the present invention, as shown in use.

In operation, it is necessary to pass fluid through the Viscometric Flowmeter 16 for initial use. Certain design features will become apparent which allow the Flowmeter to purge entrapped air by normal flow of fluid through the fluid path. It will also become apparent that as fluid is initially passed through the Flowmeter 16, it typically remains in a horizontal orientation as depicted in FIG. 1.

Figure 6:
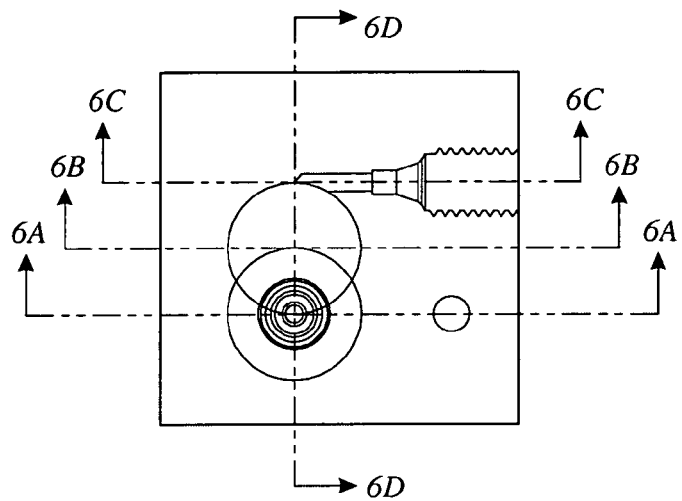
FIG. 6 with section views 6A-6D depict exploded views of the manifold(s) construction features.
Figure 6A:
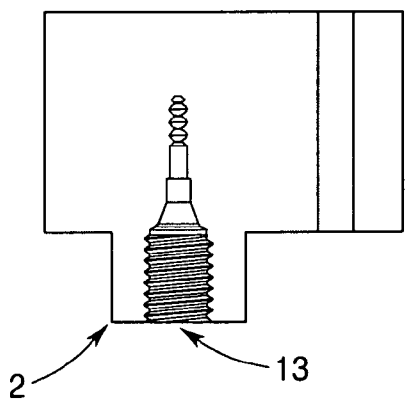
Figure 6B:
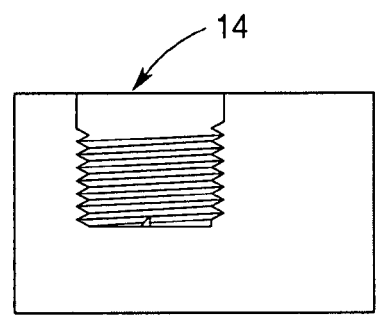
Figure 6C:
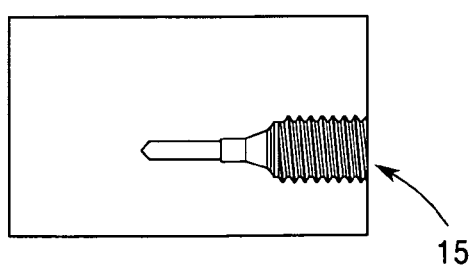

Referring now to FIG. 6, there is shown an input and output port to which tubing from external devices (e.g. pumps or columns) is connected. As fluid enters the Viscometric Flowmeter 16 through the inlet port 2, it travels into the inlet manifold 3 through the passageway 13 shown in FIG. 6A. This "passageway" is known to those skilled in the art as a 10-32 CPI (Chemical Process Industry) port 13, as is passageway 15. Again, those skilled in the art will recognize ports 13 and 15 as receptacles for compression fittings, as depicted by FIG. 17. The CPI fittings 17 are considered to be incidental hardware used as a means of connecting high pressure HPLC tubing to the 10-32 CPI ports.

Figure 6D:
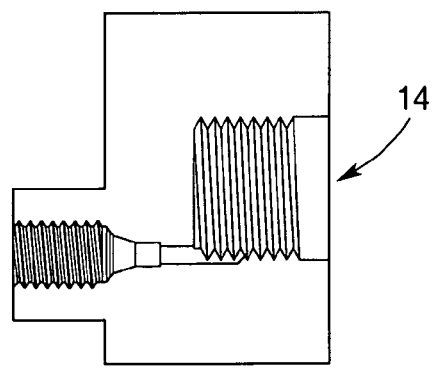

Returning to the progression of fluid into passage 13 through the inlet port 2, as fluid exits the passageway, it enters the bottom of chamber 14 depicted in FIG. 6D, which is a receptacle for the input pressure sensing transducer 4. The transducer chamber 14 intersects with ports 13 and 15 in each manifold. The input sensing transducer 4 is mounted to the inlet port 2 and converts fluid pressure at the inlet of the semi-rigid tube 1 to an electrical signal which is proportional to fluid pressure. As fluid flows into the transducer chamber 14, air is pushed ahead to the top of the chamber and fluid comes into contact with the sensing element of the pressure transducer 4. Fluid then enters passageway 15, which is located at the top of the inlet manifold 3.

Figure 4B:
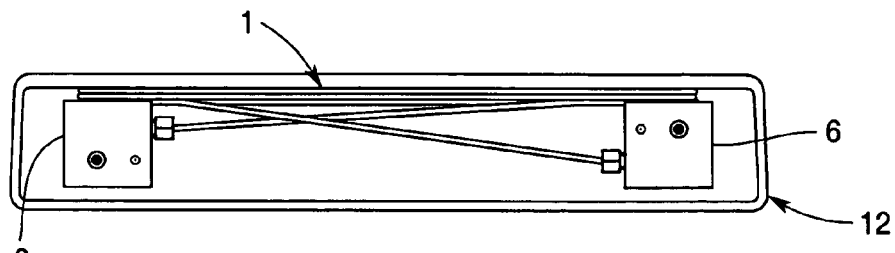
FIG. 4 with exploded views 4A, 4B, and 4C depict cross-sectional views of the present invention featuring major components except printed circuit boards.
Figure 4A:
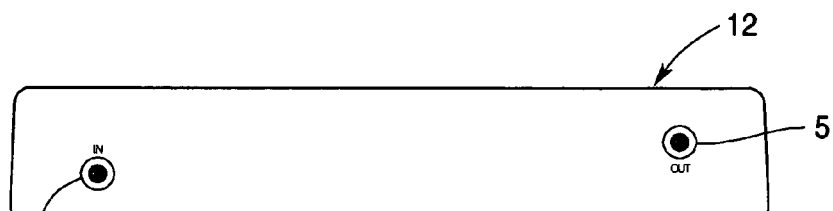
Figure 4:
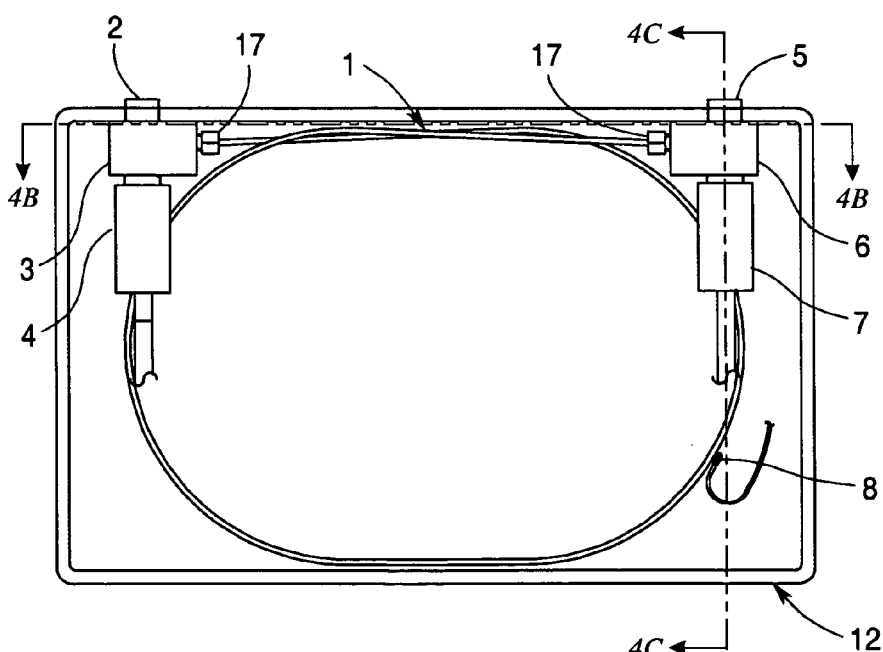
Figure 4C:
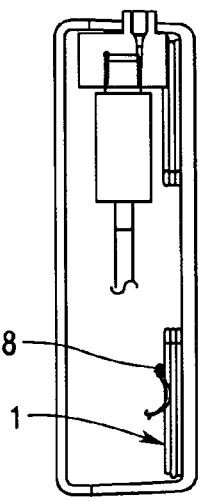

Referring now to FIG. 4, fluid enters the sense tube 1, through a compression fitting 17. Fluid flow then progresses through the tube 1, which has an inner diameter of sufficiently small size as to allow the effect of surface tension to push entrapped gasses ahead of the fluid flow. Fluid then enters the outlet manifold 6, which is functionally and mechanically similar to the inlet manifold 3, but is located at the fluid exit of the Viscometric Flowmeter. Mounted on the outlet manifold 6 is an outlet pressure sensing transducer 7 which is similar in construction to the inlet pressure transducer 4. The outlet manifold 6 is preferably mounted in an orientation which is 180 degrees rotated about the outlet port 5. The inverted mounting orientation allows port 15 on the outlet manifold 6 to serve as the fluid inlet to the manifold; in contrast to the inlet manifold, where port 15 serves as the fluid outlet from manifold 3. The use of a similar component for both the inlet and outlet manifold has the advantage of reducing the number of distinctive parts required for operation of the invention, while also providing a means to self purge.

Returning to fluid flow into the 10-32 CPI port 15 of outlet manifold 6, it should be noted that the fluid enters the transducer chamber 14 by way of its bottom section, then fills the chamber, and exits at the top of the chamber 14 through 10-32 CPI port 13. As the fluid flows through the port 13, entrapped gases are pushed ahead of the fluid in a manner similar to that of the inlet manifold 3; however, the gases travel through the port in an opposite direction due to the inverted orientation. In normal operation, tubing similar to the sense tube 1 (although not necessarily similar in inner diameter) carries fluid from the Viscometric Flowmeter 16 to the next device in the overall arrangement of the HPLC system. Having progressed through all of the fluid handling components, and purged gases from same, the system of the present invention can be oriented in positions other than horizontal provided only gas-free fluids enter the Flowmeter 16.

Having filled the Viscometric Flowmeter 16 with fluid by means of pressure applied to the fluid by an HPLC pump, and purged entrapped gases, it is now appropriate to consider the manifestation of physical forces which lead to the determination of flow. Referring to FIG. 2, fluid flows from the point of highest pressure at the outlet of the HPLC pump to the point of lowest pressure, and the Flowmeter 16 is inserted in the fluid path (immediately) after the pump, whereby fluid travels from the Flowmeter 16 through a series of tubing, fittings, or one or more LC columns, and/or other apparatus known to those skilled in the art, to a point which is at atmospheric pressure. As the fluid flows from the point of highest pressure at the pump, to a point of atmospheric pressure (typically a waste receptacle), the fluid is at an increasingly diminished pressure as it travels from the pump through the system. It follows, then, that the pressure at the fluid inlet port 2 to sense tube 1 is at a higher pressure than the pressure at the outlet port 5 of the sense tube.

It is known in the field of fluid dynamics that in the absence of turbulence, the viscosity of a liquid through a tube is given by the Hagen-Poiseuille equation:

$$\mu = \pi r^2 \Delta P T / 8 V L$$

Where:
$\mu$=shear viscosity of the fluid
$\pi$=the constant (pi) 3.14159 . . .
r=internal radius of the tube
$\Delta P$=difference in pressure drop along the length of the tube
T=time
V=volume of liquid to travel through the length of the tube
L=length of the tube Algebraic rearrangement of the terms of the equation yields:

$$V/T = \pi r^2 \Delta P / 8 \mu L$$

Where V/T (Volume per unit of time) is the flow rate.

Those skilled in the art know that high viscosity has the effect of increasing the pressure required to achieve a given flow through. It is a given that a practical flow meter must operate properly in the presence of variations in ambient temperature. Such variations can be classified as short and long term variations, where short term variations are those caused by the motion of air of various temperatures within a laboratory, which is a typical operating environment for the present invention. Such variations may be caused simply by the disturbance of air through convection, or slight breezes which result when people move about in the laboratory. Long term variations constitute those variations of the average temperature in the laboratory, as may be experienced when the temperature of the laboratory is adjusted to provide a preferred temperature for user comfort.

Short term temperature variations are partially addressed through the utilization of an enclosure 12 that protects the components of the Viscometric Flowmeter 16. The protective enclosure 12 allows the Flowmeter to maintain the temperature of the semi-rigid tube 1 at a temperature that is minimally higher than the long term ambient temperature. In addition, as fluid enters the Flowmeter 16, it encounters a thermal mass in the form of the inlet manifold 3, which taken together with the sense tube 1, and protective housing 12, act to stabilize the temperature of the fluid within the Flowmeter, and further within the sense tube. The protective enclosure may be of the commercially available molded variety, the preferred material being plastic (e.g. acrylonitrile butadiene styrene (ABS)). However, aluminum or other material capable of providing a thermal barrier against fluctuations in ambient air temperature, and supporting a display surface, may be employed.

Figure 5B:
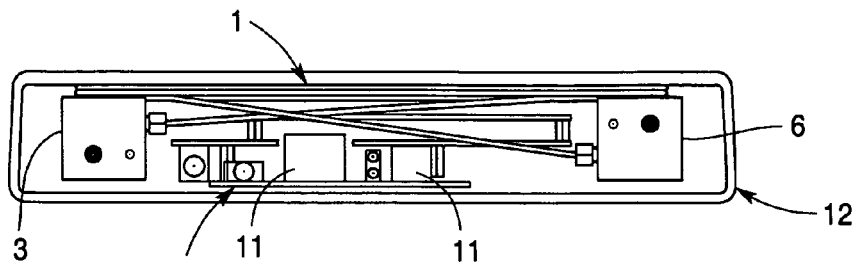
FIG. 5 with section views 5A, 5B, and 5C show the views of FIGS. 4-4C, with printed circuit boards in place.
Figure 5A:
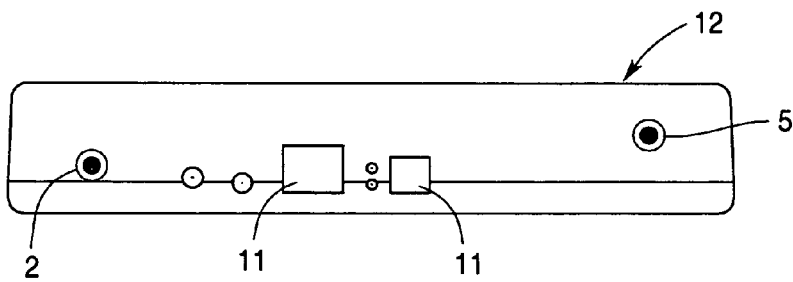
Figure 5:
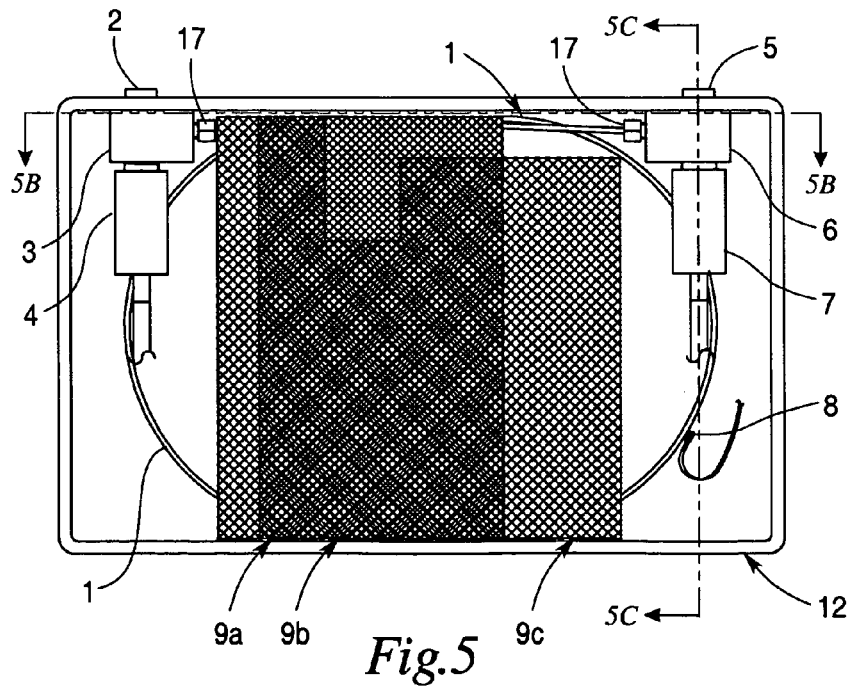
Figure 5C:
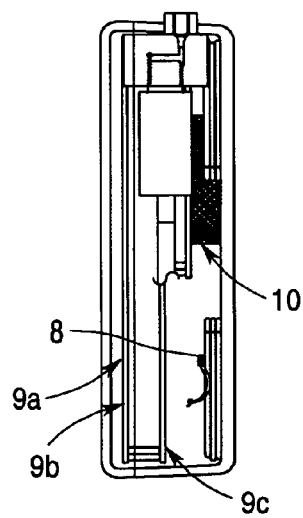

As mentioned, incoming fluids will typically be at ambient air temperature. The location of printed circuit boards 9 characteristic of this embodiment of the invention is depicted in FIG. 5. Electrical connections for conditioning signals from the inlet and outlet pressure sensing transducers 4, 7 and thermistor 8 and converting the signals to digital form are omitted for clarity. However, such circuitry may be attached to the printed circuit boards 9 by a solder connection, small electrical connector, or other mechanism known to those skilled in the art. Electronic circuitry includes, for example: (A) analog signal conditioning circuitry; (B) analog to digital conversion circuitry; (C) microcontroller or microprocessor capable of performing mathematical calculations; and (D) circuitry for communicating the formatted data to a host PC, etc.

In the illustrated embodiment, the thermistor 8 is used to determine the temperature of the fluid by indirect means through a wall of the sense tube 1, having taken care to provide an adequate thermal coupling as previously described. Printed circuit board 9C contains a microcontroller or microprocessor element which applies a viscosity correction that is specific to a particular fluid. The correction which is applied in an embodiment of the invention uses a linear interpolation between data points taken from a viscosity vs. temperature lookup table, which is specific to a particular fluid and determined using a particular method.

Advantageously, the Viscometric Flowmeter 16 of the present invention may be used in an alternative mode of operation to determine the viscosity of an unknown fluid at temperatures of interest. This method first involves using a fluid of known viscosity, HPLC grade water being a preferred fluid. Using a certified scale, or other precise device for determining the accumulation of fluid mass over time (flow rate), a constant representing the effective geometry of the sense tube 1 is recorded over a suitable range of operating pressures and temperatures. The fluid for which effective viscosity at temperature is desired is then passed through the Viscometric Flowmeter 16 at the same temperature and inlet pressure. When compared to the pressure difference produced by the fluid of known viscosity, the pressure difference of the unknown is a useful measure of the fluid's relative viscosity. Stated otherwise, the pressure difference of the two fluids can be divided to produce a ratio of viscosities, which can in turn be used to predict the performance of the unknown fluid in an HPLC or other hydraulic system. In particular, the amount of additional backpressure produced by high viscosity fluids can be estimated, and this information can be used in a predictive manner to design hydraulic systems which are less prone to failure.

The overall effect of the aforementioned method and apparatus to stabilize, control, and measure viscosity, is an increase in attainable precision and overall accuracy. A preferred embodiment of the present invention integrates firmware or other software to implement logarithmic and/or quadratic functions, to directly calculate viscosity without interpolation, to store quadratic and exponential constants specific to a particular fluid in an accessible memory location (without the need for an external programming device). Each of these features is designed to further improve the precision of the Viscometric Flowmeter 16.

Using pressure data digitized from transducers 4, 7 and temperature data digitized from transducer 8, the microprocessor on printed circuit board 9 mathematically calculates and displays the pressure(s), temperature, and instantaneous flow rate using the following relationship which has been derived (Equation 1):

$$V/T = C_t \pi^2 r^2 \Delta P_t / 8 \mu L$$

In the preceding equation, V/T (volume per unit of time) is the flow rate. $C_t$ is a mathematical function (complex or general) to adjust units of viscosity measurement and deviations in geometry of the semi-rigid tube 1. Pi or $\pi$ is the mathematical constant defining the circumference of a given perfect circle divided by its diameter. In addition, $r^2$ is the average internal radius of the sense tube squared. $\Delta P_t$ is the difference in pressure between the inlet of the sense tube 1, and the outlet. Micro or $\mu_t$ is a constant representing relative fluid viscosity, compensated for temperature. Finally, L is the length of the sense tube 1.

In practice, all geometric parameters and numeric constants are combined in a single temperature dependent term, which is typically implemented as a quadratic equation that produces suitably low errors for a given fluid. It should be noted that alternative forms of the term $C_t$ will likely be desirable as new fluids are characterized. The term $C_t$ may be, for example, non-linear, piecewise linear, or exponential. Similarly, $\mu_t$ may vary in complexity depending on the range of temperatures to be compensated over, or the nature of viscosity variation over temperature for a particular liquid.

In the present embodiment, the microprocessor 9C of the Viscometric Flowmeter 16 also calculates the deviation in flow over the last N readings using the formula:

$$D = (Max_N - Min_N)/Avg_N$$

Where:
D=deviation in flow or pressure over the last N readings.
N=programmable number of readings
$Max_N$=maximum reading during the last N readings
$Min_N$=minimum reading during the last N readings
$Avg_N$=average of the last N readings Another embodiment of the present invention uses the above-referenced method to calculate flow deviation with the additional ability to vary the time interval between samplings. This is a preferred method.

Further embodiments implement additional calculations which may be of interest to a user by appropriately modifying the firmware of the present invention.

The aforementioned data, including pressure, temperature, liquid viscosity or flow, and flow deviation, are transmitted from the computer interface connections 9 so that they can be captured, plotted, conditioned, converted, or otherwise manipulated using software for that purpose. The data is communicated to a local controller (e.g. microprocessor or micro-controller) and stored in RAM or Flash memory.

A display 10 is generally provided at the local controller for allowing a user to view pressure, temperature, flow, and other collected and derived data. The display 10 may be, for example, a plasma, liquid crystal, incandescent, LED, or other indicator or surface. A user interface 11 (e.g. keypad) may be provided for allowing data to be retrieved and/or entered by a user. Another aspect of the invention relates to the presence of standard communication ports (e.g. RS-232, USB, and Ethernet) to allow data to be transmitted electronically to and from external devices or networks. As such, the system of the present invention provides the ability to display and broadcast data that can be used for remote monitoring, remote control, and direct control (pump feedback and other hydraulic feedback) applications.

Yet another embodiment of the invention involves the use of a thermoelectric or other heating or cooling device, along with a modification of the inlet manifold 3 to force the temperature of fluid entering the semi-rigid tube 1 to a desired temperature. The effect is a simplification of the determination of viscosity vs. temperature, as viscosity will only need to be known at a single temperature, and not over a range of temperatures. This embodiment can be implemented in such a way as to provide pre-heating of fluids as may be required in certain applications.

Another aspect of the present invention relates to its ability to compare relative viscosities of fluids of differing composition. If the flow rate of an unknown solvent can be determined by other means, then the pressure differential accords a means to directly determine the relative viscosity of the unknown fluid per the modified Hagen-Poiseuille equation, previously given.

Yet another aspect of the present invention relates to its ability to control a pump by means of the RS-232 or other port. Control can be direct, as in a hardwired connection from the Viscometric Flowmeter 16 to a pump, or indirect, as through an intermediate program or software. In the indirect mode, the Flowmeter and pump may be connected through a PC, laptop, Personal Digital Assistant (PDA), or other programming device that runs the intermediate program. As an alternative, the Flowmeter 16 may be configured to communicate to a pump via a network connection such as, for example, RS-232, USB or Ethernet. In both means of connection, direct and indirect, it is possible for the apparatus to implement algorithms for issuing ever increasing or decreasing flow rate commands to a pump, which is connected to an LC or HPLC column, and then record the pressure and flow rates which result. The resultant data forms a flow vs. pressure curve, a useful tool in quality control and other evaluations of HPLC columns.

As a result, the useable life cycle of an HPLC column can be monitored and recorded by logging the pressure vs. time, total volume tally etc., wherein the Flowmeter 16 controls the source of pressure while recording the resulting flow vs. pressure characteristic.

In still another aspect of the invention, the intermediate program or software may be configured to generate a detectable signal in the event one or more measured or derived parameters from the Viscometric Flowmeter 16 deviate from a predetermined limit. These parameters include, for example, viscosity, pressure, temperature, flow direction, and flow rate. In a preferred embodiment, the detectable signal generated by the software is proportional to flow deviation. In a more preferred embodiment, the detectable signal is used to adjust precompression of a pumping mechanism (e.g. piston or linear drive pump) disposed at the inlet or outlet of the sense tube 1, so as to reduce deviation in the fluid pressure, temperature, or flow rate of an LC or HPLC system. In this fashion, data generated by the Flowmeter 16 can be used to independently validate operation of the LC system for a specified time period.

Figure 3:
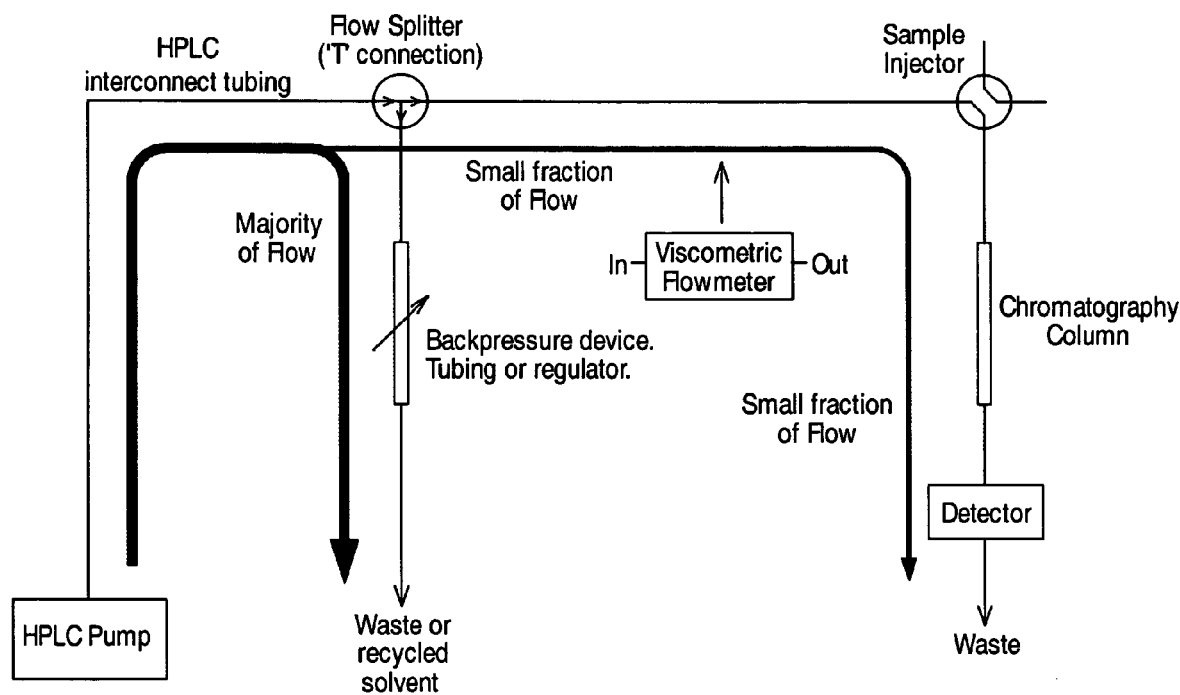
FIG. 3 is a schematic of an embodiment of the present invention in a flow splitting application.

Referring now to FIG. 3, still another embodiment of the invention features the above-mentioned direct/indirect connection means, wherein the Viscometric Flowmeter 16 maintains control of a pump, needle valve, regulator, or other backpressure regulating device, for the purpose of regulating a flow splitting topology in order to improve the accuracy of fluid delivery to the HPLC column. Stated otherwise, the Viscometric Flowmeter 16 of the present invention enables the ratio of split flows to be adjusted for changes in column backpressure.

As shown in FIG. 3, a further embodiment of the invention uses the interconnect method described previously, with the exception that instead of the Viscometric Flowmeter 16 being connected to a pump, the Flowmeter is connected to a metering valve or pressure regulator with remote control means in a flow splitting arrangement, whereby the pump operates at a more or less constant flow rate, and the rate at which fluid is delivered to the HPLC column is determined by the amount of fluid the Flowmeter 16 discharges to the waste (or recycle) receptacle by means of the backpressure regulating device, said device being controlled by the Flowmeter 16, either directly or indirectly.

In summary, by measuring or controlling the viscosity of a fluid known to be flowing through the Viscometric Flowmeter 16, the pressure drop across a sense element, combined with known or determined geometric data about the element, the present invention produces data in regard to the pressure, temperature, and most importantly, flow rate of the liquid. Such data can be used, for example, in diagnostic, fault detection, and process control applications.

It will be understood that the described arrangements of apparatus and the methods pertaining thereto are merely illustrative of applications of the principles of this invention and many other embodiments and modifications can be made by those of skill in the art without departing from the spirit and scope of the present invention.

What is claimed is:

1. A flowmeter for measuring fluid parameters in a hydraulics system, comprising:
    (a) a tube having an inlet and an outlet, and having a generally cylindrical inner geometry for building pressure proportional to flow, as a function of fluid viscosity;
    (b) a temperature transducer capable of generating a signal proportional to the temperature of said tube and a fluid within said tube;
    (c) one or more transducer disposed at the inlet and the outlet of said tube for generating a signal proportional to pressure of the fluid within said tube;
    (d) a device for digitizing the signals generated by said transducers; and
    (e) a microprocessor configured to computationally normalize the geometry of said tube and viscosity of the fluid in said tube by means of transducers wherein the following relationship holds $V/T = C_f \pi r^2 \Delta P_r / 8 \mu_r L$ where $V/T$=flow rate; $C_f$=a mathematical function to compensate flow rate for deviations of viscosity and geometry of the tube; $\pi = 3.14159\ldots$; $r^2$=average internal radius of the tube squared; $\Delta P_r$=difference in pressure between the tube inlet and the outlet; $\mu_r$=relative fluid viscosity as a function of temperature; and L=tube length.

2. The flowmeter of claim 1 further comprising a thermal mass for stabilizing the temperature of said fluid.

3. The flowmeter of claim 1 further comprising a device having an ascending fluid path for purging gas from a flow path of said fluid.

4. The flowmeter of claim 1 wherein said tube inlet or outlet comprises a manifold having an internal cavity with a radius greater than said tube to minimize relative pressure drop across the manifold.

5. The flowmeter of claim 1 wherein said flowmeter is mounted within a housing to provide a thermally insulating effect.

6. The flowmeter of claim 1 further comprising a heating or a cooling element for physically normalizing the viscosity of fluid within said tube by regulating the temperature of said fluid.

7. The flowmeter of claim 1 further comprising apparatus for storing desired operational parameters of the hydraulics system.

8. The flowmeter of claim 7 wherein said flowmeter generates a signal in the event one or more of said operational parameters deviates from a predetermined limit.

9. The flowmeter of claim 8 wherein the signal generated by said flowmeter is proportional to the level of deviation from said predetermined limit.

10. The flowmeter of claim 7 wherein said storage apparatus includes an algorithm configured to calculating deviations in short term flow rate of the fluid in said hydraulics system, in accordance with said operational parameters.

11. The flowmeter of claim 7 wherein said storage apparatus includes an algorithm configured to calculating deviations in temperature of the fluid in said hydraulics system, in accordance with said operational parameters.

12. The flowmeter of claim 7 wherein said storage apparatus includes an algorithm configured to calculating deviations in an upper pressure limit of the fluid in said hydraulics system, in accordance with said operational parameters.

13. The flowmeter of claim 1 further comprising a communications network configured to transmitting pressure, temperature, or flow rate data derived from said flowmeter to software that monitors or modulates the hydraulics system.

14. The flow meter of claim 1 whereby under normal operational conditions of an unknown but constant flow of fluid through the flowmeter and at a constant temperature, a plurality of fluids are sequentially introduced, and where the flowmeter of claim 1 configured to capture differential pressure data and store a calculated value representing a reference viscosity of the first fluid, and upon introduction of a second or third fluid, capture relative pressure data, and upon confirming identical temperature of the unknown fluid and apparatus by the microprocessor, a relative viscosity of the second or third or subsequent fluids are computed by the microprocessor.

* * * * *